(12) United States Patent
Rosenberg et al.

(10) Patent No.: US 7,846,477 B2
(45) Date of Patent: Dec. 7, 2010

(54) METHOD FOR PRODUCING SOLID GALENIC FORMULATIONS USING A CROSSLINKED NON-THERMOPLASTIC CARRIER

(75) Inventors: Jörg Rosenberg, Ellerstadt (DE); Gunther Berndl, Herxheim (DE); Markus Magerlein, Mannheim (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 488 days.

(21) Appl. No.: 10/530,483

(22) PCT Filed: Oct. 9, 2003

(86) PCT No.: PCT/EP03/11205

§ 371 (c)(1),
(2), (4) Date: Sep. 28, 2005

(87) PCT Pub. No.: WO2004/032903

PCT Pub. Date: Apr. 22, 2004

(65) Prior Publication Data

US 2006/0257470 A1    Nov. 16, 2006

(30) Foreign Application Priority Data

Oct. 9, 2002    (DE) .............................. 102 47 037

(51) Int. Cl.
*A61K 9/20*    (2006.01)
*B27N 3/00*    (2006.01)

(52) U.S. Cl. ..................... 424/464; 264/109
(58) Field of Classification Search ............... 424/464; 264/109
See application file for complete search history.

(56) References Cited

U.S. PATENT DOCUMENTS

| | | | | |
|---|---|---|---|---|
| 3,087,860 | A | * | 4/1963 | Endicott ..................... 424/419 |
| 4,632,828 | A | * | 12/1986 | Carli .......................... 514/178 |
| 4,801,460 | A | * | 1/1989 | Goertz et al. ............ 514/772.5 |
| 4,880,585 | A | | 11/1989 | Klimesch et al. |
| 4,882,144 | A | | 11/1989 | Hegasy |
| 4,892,730 | A | | 1/1990 | Hegasy |
| 4,957,681 | A | | 9/1990 | Klimesch et al. |
| 4,981,683 | A | | 1/1991 | Hegasy |
| 5,073,379 | A | * | 12/1991 | Klimesch et al. ............ 424/467 |
| RE33,963 | E | | 6/1992 | Hegasy |
| 6,290,990 | B1 | | 9/2001 | Grabowski |
| 2002/0012706 | A1 | | 1/2002 | Stergios et al. |

FOREIGN PATENT DOCUMENTS

| | | |
|---|---|---|
| CA | 2 407 063 | 10/2001 |
| EP | 0 446 753 B1 | 9/1991 |
| EP | 0 960 620 A1 | 12/1998 |
| EP | 0 960 620 | 12/1999 |
| GB | 1 442 951 | 7/1976 |
| GB | 2 153 676 A | 8/1985 |
| WO | 01 78716 | 10/2001 |

* cited by examiner

*Primary Examiner*—Robert A Wax
*Assistant Examiner*—Aradhana Sasan
(74) *Attorney, Agent, or Firm*—Novak Druce + Quigg LLP

(57) ABSTRACT

The invention concerns a method for producing solid galenic formulations which consists in: forming a processable paste comprising a) 50 to 99.4 wt. % of at least one non-thermoplastic carrier, b) 0.5 to 30 wt. % of at least an adjuvant selected among thermoplastic polymers, lipids, sugar alcohols and solubilizing agents, c) 0.1 to 49.5 wt. % of at least one active principle, at a temperature not less than the softening temperature of the adjuvant but rising to at least 70° C.; then in cooling the resulting paste. Said solid galenic formulations quickly disintegrate in an aqueous medium.

22 Claims, No Drawings

METHOD FOR PRODUCING SOLID GALENIC FORMULATIONS USING A CROSSLINKED NON-THERMOPLASTIC CARRIER

The present invention relates to a process for producing fast-release solid dosage forms.

The production of solid dosage forms by melt extrusion, i.e. a process in which a melt of a polymeric binder and of an active ingredient is extruded, and the extrudate is shaped to the desired drug form, is known, see, for example, EP-A 240 904, EP-A 240 906, EP-A 337 256 and EP-A 358 105. This process permits the preparation of slightly soluble active ingredients in the form of solid solutions. The active ingredient is present in the solid solutions in amorphous form and can therefore be absorbed more easily than the crystalline active ingredient. However, the dissolution of the dosage form and the release of the active ingredient takes place only at the surface of the dosage form. In many cases, however, rapid disintegration of the dosage form is desired.

EP-B 0078430 discloses a process for producing fast-release pharmaceutical preparations comprising dihydropyridine, polyvinylpyrrolidone and insoluble carriers such as crosslinked polyvinylpyrrolidone, where the active ingredient and the polyvinylpyrrolidone are dissolved in an organic solvent, and the solution is granulated with the carrier. This process cannot, however, be directly applied to other slightly soluble active ingredients because a suitable physiologically tolerated solvent does not exist for all active ingredients and/or complete removal of the solvent is impossible or possible only in a troublesome manner.

GB 2 153 676 proposes the loading of water-insoluble polymers such as crosslinked polyvinylpyrrolidone with an active ingredient by mixing the polymer with the active ingredient and heating to the melting point of the active ingredient. This procedure has the disadvantage that many active ingredients cannot be melted without decomposition.

EP-A 0 446 753 discloses the loading of crosslinked polymers with an active ingredient by treating the polymer with a solution of the active ingredient, or grinding the polymer and the active ingredient with high energy input. The process has the disadvantage that it cannot be carried out continuously.

DE-A 44 13 350 describes slow-release matrix pellets consisting of an active ingredient, 5 to 50% by weight of a water-insoluble polymer such as ethylcellulose, 5 to 45% by weight of a lipophilic component, 3 to 40% by weight of a gel former such as hydroxypropylcellulose, and where appropriate formulation aids. The slow-release matrix pellets can be produced by melt extrusion.

It is an object of the invention to indicate a universally applicable process which allows dosage forms with rapid release in particular of slightly soluble active ingredients to be produced without the need to use organic solvents or to melt the active ingredient.

The present invention therefore relates to a process for producing solid dosage forms, in which a moldable composition which comprises
a) 50 to 99.4% by weight, preferably 60 to 80% by weight, of at least one crosslinked nonthermoplastic carrier,
b) 0.5 to 30% by weight, preferably 5 to 20% by weight, of at least one adjuvant selected from thermoplastic polymers, lipids, sugar alcohols, sugar alcohol derivatives and solubilizers and
c) 0.1 to 49.5% by weight, preferably 5 to 25% by weight, of at least one active ingredient, is formed at a temperature at or above the softening point of the adjuvant, but at least 70° C., preferably 100 to 180° C., and subsequently cooled.

In preferred embodiments, the composition comprises
a) 50 to 90% by weight, preferably 60 to 80% by weight, of at least one crosslinked nonthermoplastic carrier,
b1) 5 to 30% by weight, preferably 7 to 15% by weight, of at least one thermoplastic polymer,
b2) 0.5 to 20% by weight, preferably 5 to 10% by weight, of at least one solubilizer,
c) 0.1 to 45.5% by weight, preferably 5 to 25% by weight, of at least one active ingredient.

The crosslinked nonthermoplastic carrier acts as disintegrant which brings about rapid disintegration of the dosage form in an aqueous environment such as gastric juice. It is surprisingly possible to produce the dosage forms, which comprise a predominant proportion of a crosslinked nonthermoplastic carrier, in the absence of solvents through a process similar to melt extrusion if particular adjuvants are additionally used. "Adjuvant" or "adjuvants" mean excipients which remain in the dosage form and are not merely added during production and are removed again in a later processing step.

Dosage forms mean all forms suitable for use as medicaments, in particular for oral administration, plant-treatment compositions, animal feeds and dietary supplements. They include for example tablets of any shape, pellets or granules.

The crosslinked nonthermoplastic carrier is a natural, semisynthetic or fully synthetic polymer which is crosslinked to a degree of crosslinking such that it has no thermoplastic properties. It is usually insoluble in water but swellable in water. The nonthermoplastic carrier is preferably selected from crosslinked polyvinylpyrrolidone and crosslinked sodium carboxymethylcellulose. Crosslinked polyvinylpyrrolidone is most preferred. Suitable products are described for example in the US Pharmacopeia (USP NF).

Besides the active ingredient and the crosslinked nonthermoplastic carrier, there is also employed in the process of the invention at least one adjuvant selected from thermoplastic polymers, lipids, sugar alcohols, sugar alcohol derivatives and solubilizers.

Examples of suitable thermoplastic polymers are polyvinylpyrrolidone (PVP), copolymers of N-vinylpyrrolidone and vinyl acetate or vinyl propionate, copolymers of vinyl acetate and crotonic acid, partially hydrolyzed polyvinyl acetate, polyvinyl alcohol, polyhydroxyalkylacrylates, polyhydroxyalkyl-methacrylates, polyacrylates and polymethacrylates (Eudragit types), copolymers of methyl methacrylate and acrylic acid, polyethylene glycols, alkylcelluloses, especially methylcellulose and ethylcellulose, hydroxyalkylcelluloses, especially hydroxypropylcellulose (HPC), hydroxyalkylalkylcelluloses, especially hydroxypropylmethylcellulose (HPMC), cellulose esters such as cellulose phthalates, in particular cellulose acetate phthalate, hydroxypropylmethylcellulose phthalate and hydroxypropylmethylcellulose acetate succinate (HPMCAS). Of these, homo- or copolymers of vinylpyrrolidone are particularly preferred, e.g. polyvinylpyrrolidone with Fikentscher K values of from 12 to 100, preferably 17 to 30, or copolymers of 30 to 70% by weight of N-vinylpyrrolidone (VP) and 70 to 30% by weight of vinyl acetate (VA), such as, for example, a copolymer of 60% by weight VP and 40% by weight VA.

The thermoplastic polymers preferably have a softening temperature of from 60 to 180° C., in particular 70 to 130° C.

Suitable sugar alcohols are sorbitol, xylitol, mannitol, maltitol; a suitable sugar alcohol derivative is isomalt.

Suitable lipids are fatty acids such as stearic acid; fatty alcohols such as cetyl or stearyl alcohol; fats such as animal or vegetable fats; waxes such as carnauba wax; or mono- and/or diglycerides or phosphatides, especially lecithin. The fats preferably have a melting point of at least 50° C. Triglycerides of $C_{12}$, $C_{14}$, $C_{16}$ and $C_{18}$ fatty acids are preferred.

Solubilizers mean pharmaceutically acceptable nonionic surface-active compounds. Suitable solubilizers include sorbitan fatty acid esters, polyalkoxylated fatty acid esters such as, for example, polyalkoxylated glycerides, polyalkoxylated sorbitan fatty acid esters or fatty acid esters of polyalkylene glycols; or polyalkoxylated ethers of fatty alcohols. A fatty acid chain in these compounds usually comprises 8 to 22 carbon atoms. The polyalkylene oxide blocks comprise on average from 4 to 50 alkylene oxide units, preferably ethylene oxide units, per molecule.

Suitable sorbitan fatty acid esters are sorbitan monolaurate, sorbitan monopalmitate, sorbitan monostearate, sorbitan monooleate, sorbitan tristearate, sorbitan trioleate, sorbitan monostearate, sorbitan monolaurate or sorbitan monooleate.

Examples of suitable polyalkoxylated sorbitan fatty acid esters are polyoxyethylene(20)sorbitan monolaurate, polyoxyethylene (20)sorbitan monopalmitate, polyoxyethylene (20)sorbitan monostearate, polyoxyethylene(20)sorbitan monooleate, polyoxyethylene(20)sorbitan tristearate, polyoxyethylene(20)sorbitan trioleate, polyoxyethylene(4)sorbitan monostearate, polyoxyethylene(4)sorbitan monolaurate or polyoxyethylene(4)sorbitan monooleate.

Suitable polyalkoxylated glycerides are obtained for example by alkoxylation of natural or hydrogenated glycerides or by transesterification of natural or hydrogenated glycerides with polyalkylene glycols. Commercially available examples are polyoxyethylene glycerol ricinoleate 35, polyoxyethylene glycerol trihydroxystearate 40 (Cremophor® RH40, BASF AG) and polyalkoxylated glycerides obtainable under the proprietary names Gelucire® and Labrafil® from Gattefosse, e.g. Gelucire® 44/14 (lauroyl macrogol 32 glycerides prepared by transesterification of hydrogenated palm kernel oil with PEG 1500), Gelucire® 50/13 (stearoyl macrogol 32 glycerides prepared by transesterification of hydrogenated palm oil with PEG 1500) or Labrafil M1944 CS (oleoyl macrogol 6 glycerides prepared by transesterification of apricot kernel oil with PEG 300).

A suitable fatty acid ester of polyalkylene glycols is for example PEG 660 hydroxystearic acid (polyglycol ester of 12-hydroxystearic acid (70 mol %) with 30 mol % ethylene glycol).

Suitable polyalkoxylated ethers of fatty alcohols are for example macrogol 6 cetylstearyl ether or macrogol 25 cetylstearyl ether Besides these, it is possible additionally to use conventional pharmaceutical excipients, the total amount of which may be up to 20% by weight based on the dosage form. These include:

extenders or fillers such as lactose, cellulose, silicates or silica, lubricants such as magnesium stearate and calcium stearate, sodium stearyl fumarate, colorants such as azo dyes, organic or inorganic pigments or colorants of natural origin, stabilizers such as antioxidants, light stabilizers, hydroperoxide destroyers, radical scavengers, stabilizers against microbial attack.

Active ingredients mean for the purposes of the invention all substances with a desired physiological effect on the human or animal body or plants. They are in particular active pharmaceutical ingredients. The amount of active ingredient per dose unit may vary within wide limits. It is usually chosen so that it is sufficient to achieve the desired effect. Combinations of active ingredients can also be employed. Active ingredients for the purposes of the invention are also vitamins and minerals. Vitamins include the vitamins of the A group, or the B group, by which are meant besides $B_1$, $B_2$, $B_6$ and $B_{12}$ and nicotinic acid and nicotinamide also compounds having vitamin B properties such as, for example, adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group. Active ingredients for the purposes of the invention also include peptide therapeutics and proteins. Plant treatment agents include for example vinclozolin, epoxiconazole and quinmerac.

The process of the invention is suitable, for example, for processing the following active ingredients:

acebutolol, acetylcysteine, acetylsalicylic acid, acyclovir, albrazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkonium hydrochloride, benzocaine, benzoic acid, betamethasone, bezafibrate, biotin, biperidene, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefatroxil, cefazolin, cefixime, cefotaxime, ceftazidime, ceftriaxone, cefuroxime, celedilin, chloramphenicol, chlorhexidine, chlorpheniramine, chlortalidone, choline, cyclosporin, cilastatin, cimetidine, ciprofloxacin, cisapride, cisplatin, clarithromycin, clevulanic acid, clomibramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphen, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus Globulus, famotidine, felodipine, fenofibrate, fenofibric acid, fenoterol, fentanyl, flavin mononucleotide, fluconazole, flunarizine, fluorouracil, fluoxetine, flurbiprofen, furosemide, gallopamil, gemfibrozil, gentamicin, Gingko Biloba, glibenclamide, glipizide, clozapine, Glycyrrhiza glabra, griseofulvin, guaifenesin, haloperidol, heparin, hyaluronic acid, hydrochlorothiazide, hydrocodone, hydrocortisone, hydromorphone, ipratropium hydroxide, ibuprofen, imipenem, indomethacin, insulin, iohexol, iopamidol, isosorbide dinitrate, isosorbide mononitrate, isotretinoin, ketotifen, ketoconazole, ketoprofen, ketorolac, labatalon, lactulose, lecithin, levocarnitine, levodopa, levoglutamide, levonorgestrel, levothyroxine, lidocaine, lipase, lipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures or combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, phenobarbital, phenoxifylline, phenoxymethylpenicillin, phenylephrine, phenylpropanolamine, phenyloin, piroxicam, polymyxin B, povidone-iodine, pravastatin, prazepam, prazosin, prednisolone, prednisone, promocriptine, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamteren, trimethoprim, troxerutin, uracil, valproic acid, vancomycin, verapamil, vitamin E, volinic acid, zidovudine.

The process is particularly suitable for active ingredients having a solubility in water at 25° C. of less than 1 mg/ml. Such active ingredients are also referred to according to USP XXII, page 8, as scarcely soluble or practically insoluble.

The solid dosage forms are produced by producing, at an elevated temperature, i.e. a temperature at or above the softening point of the adjuvant, but at least 70° C., a moldable cohesive composition of the components, which is subsequently cooled, where appropriate after a shaping step. The time for which the components are exposed to the elevated temperature is preferably less than 5 minutes, in particular less than 3 minutes, for each of the components.

The mixing of the components and the formation of the moldable composition can take place in various ways. The mixing can take place before, during and/or after the heating of one or all of the components of the composition, although it is not expedient to heat the crosslinked nonthermoplastic carrier in the absence of the thermoplastic components of the composition. For example, the components can first be mixed and then heated to form the moldable composition. However, they can also be mixed and heated simultaneously. The moldable composition is frequently also homogenized in order to obtain a highly dispersed distribution of the active ingredient. In the case of sensitive active ingredients, preferably the adjuvant(s) is (are) initially melted in the presence of the nonthermoplastic carrier and then the active ingredient is admixed.

The heating takes place in an apparatus usual for this purpose. Heatable extruders or kneaders are particularly suitable, such as mixer/kneader reactors (e.g. ORP, CRP, AP, DTB supplied by List or Reactotherm supplied by Krauss-Maffei or Ko-kneader supplied by Buss), trough mixers and internal mixers or rotor/stator systems (e.g. Dispax supplied by IKA). The residence time of the composition in the extruder is preferably less than 5 minutes, in particular less than 3 minutes.

Extruders which can be employed are single-screw machines, intermeshing screw machines or else multi-screw extruders, especially twin screw extruders, corotating or counter-rotating and, where appropriate, equipped with kneading disks. Twin screw extruders of the ZSK series from Werner & Pfleiderer are particularly preferred.

The charging of the extruder or kneader takes place continuously or batchwise according to the design thereof in a conventional way. Powdered components can be fed in freely, e.g. via a weigh feeder. Plastic compositions can be fed in directly from an extruder or fed in via a gear pump, which is particularly advantageous for high viscosities and high pressures. Liquid media can be metered in via a suitable pumping unit.

The resulting composition is doughy or pasty. It is usually subjected to a shaping. It is possible in this way to produce a large number of shapes, depending on the tool and mode of shaping. For example, on use of an extruder the extrudate can be shaped between a belt and a roll, between two belts or between two rolls, as described in EP-A-358 105, or by calendering in a calender with two molding rolls, see, for example, EP-A-240 904. Small-particle granules can be obtained for example by extrusion and hot or cold cut of the extrudate. The cooled compositions can then also be ground to a powder and subsequently compressed to tablets in a conventional way. It is possible in this case also to use tableting aids such as colloidal silica, calcium hydrogen phosphate, lactose, microcrystalline cellulose, starch or magnesium stearate.

The invention is illustrated in more detail by the following examples.

EXAMPLES

Example 1

A mixture of 20.83% by weight of active ingredient (lopinavir), 68.17% by weight of crosslinked polyvinylpyrrolidone (Kollidon CL), 7.00% by weight of polyoxyethylene glycerol trihydroxystearate 40 (Cremophor® RH-40) and 1.00 by weight of Aerosil 200 was processed in a twin screw extruder (18 mm screw diameter) at a material temperature of 120° C. The Cremophor® RH-40 had previously been mixed at room temperature with the powdered Kollidon CL with stirring or kneading to give free-flowing granules, to which the active ingredient and the Aerosil 200 were then admixed. 1.5 kg/h of this mixture were then fed via a weigh feeder into the extruder. A hot moldable composition in the form of a white extrudate emerged from the extruder head and then hardened after cooling. The cooled extrudates (with a thickness of about 10 mm) disintegrated in water within a few minutes.

Example 2

Pieces of the extrudate obtained in example 1 were ground in a laboratory mill (from Retsch) and, after addition of 12% by weight of calcium hydrogen phosphate and 1% by weight of Aerosil 200 (colloidal silica), compressed in an eccentric press (Fette E 1) to oblong tablets. The tablets showed a disintegration time of a few minutes in a disintegration test (complying with DAB) in 0.1 M hydrochloric acid at 37° C.

Example 3

Comparative Example

Example 1 was repeated but with use of a copolymer of 60% by weight of N-vinylpyrrolidone and 40% by weight of vinyl acetate (Kollidon VA-64) instead of Kollidon CL. A translucent extrudate emerged from the extruder head and formed a hard brittle composition after cooling. The extrudates dissolved in water only after several hours.

Example 4

Comparative Example

Pieces of the extrudate obtained in example 3 were ground in analogy to example 2 and compressed with the stated excipients to oblong tablets. The disintegration time of the tablets in a disintegration test (complying with DAB) was more than 3 hours.

Example 5

A mixture of 20.83% by weight of active ingredient (lopinavir), 61.17% by weight of crosslinked polyvinylpyrrolidone (Kollidon CL), 10.00% by weight of N-vinylpyrrolidone/vinyl acetate 60/40 copolymer (Kollidon VA-64), 7.00% by weight of Cremophor RH-40 and 1.00 by weight of Aerosil 200 was processed in analogy to example 1. A hot moldable composition in the form of a white extrudate emerged from the extruder head and hardened after cooling. The cooled extrudates disintegrated in water in a few minutes.

Example 6

A mixture of 20.83% by weight of active ingredient (lopinavir), 51.17% by weight of crosslinked polyvinylpyrrolidone (Kollidon CL), 20.00% by weight of N-vinylpyrrolidone/vinyl acetate 60/40 copolymer (Kollidon VA-64), 7.00% by weight of Cremophor RH-40 and 1.00 by weight of Aerosil 200 was processed in analogy to example 1. A hot moldable composition in the form of a yellowish white extrudate emerged from the extruder head and hardened after cooling. The cooled extrudates disintegrated in water in a few minutes.

Example 7

A mixture of 20.83% by weight of active ingredient (lopinavir), 61.17% by weight of crosslinked polyvinylpyrrolidone (Kollidon CL), 10.00% by weight of N-vinylpyrrolidone/vinyl acetate 60/40 copolymer (Kollidon VA-64), 7.00% by weight of sorbitan monopalmitate (Span 40) and 1.00 by weight of Aerosil 200 was processed in analogy to example 1. A hot moldable composition in the form of a yellowish white extrudate emerged from the extruder head and hardened after cooling. The cooled extrudates disintegrated in water in a few minutes.

We claim:

1. A process for producing solid dosage forms, comprising
   (i) forming a moldable cohesive composition which comprises
      a) 50 to 99.4% by weight of at least one crosslinked nonthermoplastic carrier,
      b) 0.5 to 30% by weight of at least one adjuvant selected from the group consisting of thermoplastic polymers, lipids, sugar alcohols, sugar alcohol derivatives and solubilizers and
      c) 0.1 to 49.5% by weight of at least one active ingredient, by heating at a temperature at or above the softening point of the adjuvant, but at least 70° C., in a multi-screw extruder, and
   (ii) subsequently cooling the moldable composition to form the solid dosage forms.

2. The process according to claim 1, where the composition comprises
   a) 50 to 90% by weight of at least one crosslinked nonthermoplastic carrier,
   b1) 5 to 30% by weight of at least one thermoplastic polymer,
   b2) 0.5 to 20% by weight of at least one solubilizer,
   c) 0.1 to 45.5% by weight of at least one active ingredient.

3. The process according to claim 1, where the crosslinked nonthermoplastic carrier is selected from the group consisting of crosslinked polyvinylpyrrolidone, crosslinked sodium carboxymethylcellulose and mixtures thereof.

4. The process according to claim 1, where the thermoplastic polymer is a homo- or copolymer of vinylpyrrolidone.

5. The process according to claim 1, where the sugar alcohol is selected from the group consisting of sorbitol, xylitol, mannitol, maltitol, the sugar alcohol derivative isomalt and mixtures thereof.

6. The process according to claim 1, where the lipid is selected from the group consisting of fatty acids, fatty alcohols, fats, waxes, mono- and diglycerides, phosphatides and mixtures thereof.

7. The process according to claim 1, where the solubilizer is selected from the group consisting of sorbitan fatty acid esters, polyalkoxylated fatty acid esters, polyalkoxylated ethers of fatty alcohols and mixtures thereof.

8. The process according to claim 1, where the active ingredient has a solubility in water at 25° C. of less than 1 mg/ml.

9. The process according to claim 1, where the cooled composition is comminuted and compressed to the dosage form.

10. The process according to claim 9, wherein at least one tableting aid is employed, and wherein the at least one tableting aid is selected from the group consisting of colloidal silica, calcium hydrogen phosphate, lactose, microcrystalline cellulose, starch, and magnesium stearate.

11. The process according to claim 1, wherein components a)-c) are mixed before heating.

12. The process according to claim 1, wherein components a)-c) are mixed during heating.

13. The process according to claim 1, wherein components a)-c) are mixed after heating at least one of the components.

14. The process according to claim 1, wherein the moldable cohesive composition is homogenized to distribute the active ingredient.

15. The process according to claim 1, further comprising melting the at least one adjuvant in the presence of the nonthermoplastic carrier, and admixing the active ingredient, wherein the steps of melting and admixing are carried out prior to the step of forming the moldable cohesive composition.

16. The process according to claim 1, wherein the composition remains in the multi-screw extruder for a residence time of less than 5 minutes.

17. The process according to claim 1, wherein the composition remains in the multi-screw extruder for a residence time of less than 3 minutes.

18. The process according to claim 1, further comprising shaping the moldable cohesive composition between at least one belt and at least one roll.

19. The process according to claim 1, further comprising shaping the moldable cohesive composition by calendaring in a calendar with two molding rolls.

20. The process according to claim 1, further comprising extruding the moldable composition, and hot or cold cutting to form small-particle granules.

21. The process according to claim 1, wherein the temperature is from 70° C. -180° C.

22. The process according to claim 1, wherein the process is carried out in the absence of a solvent.

\* \* \* \* \*